United States Patent
Kapur et al.

(10) Patent No.: US 10,733,683 B2
(45) Date of Patent: Aug. 4, 2020

(54) SYSTEM AND METHOD OF FACILITATING THE COORDINATION OF BENEFITS FOR A PLURALITY OF HEALTH PLANS

(71) Applicant: Council for Affordable Quality Healthcare, Inc., Washington, DC (US)

(72) Inventors: Akshay Kapur, Chicago, IL (US); Atul Pathiyal, Washington, DC (US)

(73) Assignee: Council for Affordable Quality Healthcare, Inc., Washington, DC (US)

( * ) Notice: Subject to any disclaimer, the term of this patent is extended or adjusted under 35 U.S.C. 154(b) by 816 days.

(21) Appl. No.: 14/212,321

(22) Filed: Mar. 14, 2014

(65) Prior Publication Data
US 2014/0278501 A1   Sep. 18, 2014

Related U.S. Application Data

(60) Provisional application No. 61/801,031, filed on Mar. 15, 2013.

(51) Int. Cl.
*G06Q 50/22* (2018.01)
*G06Q 10/10* (2012.01)
*G06F 19/00* (2018.01)

(52) U.S. Cl.
CPC .......... *G06Q 50/22* (2013.01); *G06F 19/328* (2013.01); *G06Q 10/10* (2013.01)

(58) Field of Classification Search
CPC ....... G06Q 50/22; G06Q 10/10; G06F 19/328
USPC .......................................................... 705/2
See application file for complete search history.

(56) References Cited

U.S. PATENT DOCUMENTS

| | | | |
|---|---|---|---|
| 7,133,840 B1* | 11/2006 | Kenna et al. | 705/35 |
| 7,788,115 B2 | 8/2010 | Flam et al. | 705/4 |
| 7,805,322 B2 | 9/2010 | Flam et al. | 705/4 |
| 8,103,527 B1* | 1/2012 | Lasalle | G06Q 40/08 705/35 |
| 8,260,634 B1* | 9/2012 | Lawlor | G06Q 50/18 705/2 |
| 8,321,243 B1* | 11/2012 | Harris, Sr. | G06Q 10/10 705/3 |
| 2004/0172313 A1 | 9/2004 | Stein et al. | 705/4 |
| 2005/0288972 A1 | 12/2005 | Marvin et al. | 705/4 |
| 2007/0050219 A1* | 3/2007 | Sohr | G06Q 40/08 705/4 |

(Continued)

*Primary Examiner* — Hiep V Nugyen
(74) *Attorney, Agent, or Firm* — Sheppard Mullin Richter & Hampton LLP

(57) ABSTRACT

The disclosure relates to systems and methods of facilitating the coordination of benefits for a plurality of health plans that individually have at least some responsibility to pay for healthcare services received by members covered by more than one health plan. The coordination of benefits may be facilitated before payments are made, streamlining the payment process. The system may correlate health plan information received from various health plans and determine that a particular member is covered by more than one health plan based on the correlated health plan information. The system may generate, update, and provide a COB registry that includes coverage information related to other health plans that cover the particular member. The COB registry may include primacy information used to identify health plans having primary, secondary, and/or other responsibility to pay for a given healthcare service for a member covered by the identified health plans.

28 Claims, 6 Drawing Sheets

(56) References Cited

U.S. PATENT DOCUMENTS

| | | | |
|---|---|---|---|
| 2007/0192146 A1 | 8/2007 | Menocal et al. | 705/4 |
| 2009/0055225 A1* | 2/2009 | Russell | G06Q 10/087 705/4 |
| 2009/0234670 A1 | 9/2009 | Larsen | 705/2 |

* cited by examiner

SYSTEM AND METHOD OF FACILITATING THE COORDINATION OF BENEFITS FOR A PLURALITY OF HEALTH PLANS

CROSS-REFERENCE TO RELATED APPLICATIONS

This Application claims priority to U.S. Provisional Patent Application Ser. No. 61/801,031, filed Mar. 15, 2013, which is hereby incorporated by reference herein in its entirety.

FIELD OF THE INVENTION

The disclosure relates to systems and methods of facilitating the coordination of benefits for a plurality of health plans that individually have at least some responsibility to pay for healthcare services received by members covered by more than one health plan.

BACKGROUND OF THE INVENTION

A health plan may agree to at least partially pay for one or more healthcare services obtained by a covered member. For example, the health plan may include a health insurance plan, a health maintenance organization plan, and/or other type of plan that imposes at least some responsibility to pay for healthcare services obtained by a covered member. The health plan may include public and/or private plans provided by public or private entities. For example, a health plan may include a government health plan (e.g., a U.S. Federal provider such as Medicare or a local government health plan) and/or a private provider of a private health plan.

A member may include one or more individuals or entities covered by a health plan. A given member may be covered by two or more health plans. In such a case, the two or more health plans may individually have primary, secondary, and/or other responsibility to pay for healthcare services received by the given member. The different levels of responsibility can cause problems.

For example, members may conventionally provide a healthcare service provider such as a physician, dentist, hospitals, labs, DME vendors, etc., with health plan information such as a health plan identification that identifies the health plan. Oftentimes, the provided information is incorrect or incomplete, causing the healthcare service provider to incorrectly request payment from a secondary health plan rather than a primary health plan that should have been billed or to request payment from a single health plan when a secondary health plan should also share in the payment. Even when payment requests are submitted to the proper health plan, correctly apportioning the payment among the primary and secondary health plans can be problematic. Oftentimes one health plan is unaware that the member is also covered by another health plan and the details of the other health plan are unknown.

When other health plans are identified, apportioning payment responsibility is oftentimes performed incorrectly because appropriate primacy information that indicates payment responsibilities is unavailable, unknown, or is misinterpreted. Such apportionment can also be performed after one of the health plans has already paid for the healthcare service, causing further inefficiencies of conventional systems and methods. These and other inefficiencies result in higher costs for several parties involved, from healthcare service providers to health plans.

SUMMARY OF THE INVENTION

The disclosure relates to systems and methods of facilitating the coordination of benefits for a plurality of health plans that individually have at least some responsibility to pay for healthcare services received by members covered by more than one health plan, according to an aspect of the invention.

According to an aspect of the invention, a system may include a Coordination of Benefits ("COB") computer having one or more processors configured (e.g., programmed) with one or more computer program modules. The COB computer may be configured to obtain health plan information that includes member information and coverage information. Member information may include information for identifying a given member and determining the relationship between multiple members (e.g., a subscriber and a dependent of the subscriber). Coverage information may include information that describes a health plan such as coverage limits, deductibles, and/or other coverage provided by the health plan. The health plan information may be obtained from different health plans that provide member and coverage information related to their respective members. The COB computer may determine that a particular member is covered by more than one health plan based on the health plan information.

According to an aspect of the invention, the COB computer may be configured to facilitate the coordination of benefits by generating, updating, and providing a COB registry that includes, for a given member, an identification of one or more health plans that cover the given member. For example, the COB computer may be configured to associate a given member with two or more sets of health plan information that individually describe different health plans that cover the given member. The COB computer may do so based on exact or inexact member matching using member information included in the different sets of health plan information.

According to an aspect of the invention, the COB computer may be configured to include primacy information with the COB registry. The primacy information may be used to identify health plans having primary, secondary, and/or other responsibility to pay for a given healthcare service for a member covered by the identified health plans. The primacy information enables health plans and others to identify who should pay for healthcare services. If the primacy information includes apportionment information that indicates how a given cost for a healthcare service should be apportioned to different health plans, then the COB computer may determine an appropriate ratio or percentage (including 0-100%) for individual health plans that cover a member.

According to an aspect of the invention, the computer may be configured to provide relevant portions of the COB registry for generating local COB registries. An individual local COB registry may have its own relevant portion of the COB registry such that a recipient of the relevant portion has only information about members that is relevant to the recipient. For example, a health plan may obtain health plan information of other health plans that cover its members. In this manner, a given health plan may identify other health plans that cover the given member before payments are made in relation to healthcare services received by the given member.

According to an aspect of the invention, the COB computer may be configured to facilitate inquiry/response messaging, such as conventional 270/271 inquiry/response messaging, between various users, which may include health plans, healthcare service providers, members, and/or other users. The COB computer may facilitate inquiry/response messaging by providing a platform by which information from the COB registry may be used by the various users to exchange and request information. The COB computer may also mediate inquiry/response messaging between the various users by serving as an intermediary to one or more message clearinghouses, practice management systems or other healthcare technology service providers. The inquiry/response messages may be used to share health plan information, request billing information, request eligibility information, confirm/deny billing information, confirm/deny eligibility information, and/or otherwise facilitate communication between various users.

In some implementations, the COB computer may facilitate identification of a health plan that covers a member but was previously unknown. For example, a patient may inform a healthcare service provider that the patient is covered by a first health plan. The healthcare service provider may send an inquiry message (whether 270/271 messages or not) to a clearinghouse to inquire about eligibility and/or payment. The clearinghouse may forward the inquiry to both the first health plan and the COB computer. The first health plan may response with eligibility or other information. The COB computer may respond that a second health plan also provides coverage for the patient and optionally may also include primacy and/or coverage information if available. The clearinghouse may forward both responses to the healthcare service provider, thereby informing the provider that the patient is also covered by the second health plan.

A given healthcare service provider may benefit from using the system by obtaining information that facilitates identification of primary, secondary, and/or other responsible health plans provided to the member. In this manner, the healthcare service provider may obtain accurate and updated health plan information related to members (e.g., patients of the healthcare service provider). The healthcare service provider may then obtain eligibility information, confirm primacy, confirm secondary coverage, bill (e.g., request payment from) the appropriate one or more health plans, and/or otherwise improve efficiency of office operations.

A given health plan may benefit from using the system by obtaining information about another health plan that also covers one of its members based on the COB registry. The given healthcare provider may therefore obtain information that is used to determine whether the given health plan has primary responsibility to pay for a particular healthcare service, whether primary responsibility for payment rests on another health plan, or whether the particular healthcare service has secondary or other responsibility (including no responsibility) to pay for the particular healthcare service. A health plan may use the COB registry for support in claim processing and supporting appeal resolution (e.g., when a provider or a covered member appeals a decision with respect to coverage).

A healthcare service provider and/or a health plan may therefore use relevant portions of the COB registry provided by the system to identify health plans having various responsibilities for paying for healthcare services provided to members covered by two or more health plans. The system may provide relevant portions of the COB registry prior to payments being made by health plans, thereby allowing upfront indications of which health plan should pay for a given expense related to healthcare services obtained by a member who is covered by more than one health plan.

These and other objects, features, and characteristics of the system and/or method disclosed herein, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION OF THE INVENTION

The disclosure relates to systems and methods of facilitating the coordination of benefits for a plurality of health plans that individually have at least some responsibility to pay for healthcare services received by members covered by more than one health plan, according to an aspect of the invention. For example, a system may correlate health plan information received from various health plans and determine that a particular member is covered by more than one health plan based on the correlated health plan information. The system may facilitate the coordination of benefits by generating, updating, and providing a COB registry that includes coverage information for the member, including coverage information related to other health plans that cover the particular member. The COB registry may include primacy information used to identify health plans having primary, secondary, and/or other responsibility to pay for a given healthcare service for a member covered by the identified health plans.

A given healthcare service provider may benefit from the system by obtaining information that facilitates identification of primary, secondary, and/or other responsible health plans provided to the member. The healthcare service provider may then bill (e.g., request payment from) the appropriate one or more health plans.

A given health plan may benefit from the system by obtaining information about another health plan that also covers one of its members based on the COB registry. The given healthcare provider may therefore obtain information that is used to determine whether the given health plan has primary responsibility to pay for a particular healthcare service, whether primary responsibility for payment rests primarily on another health plan, or whether the particular healthcare service has secondary or other responsibility (including no responsibility) to pay for the particular healthcare service.

A healthcare service provider and/or a health plan may therefore use relevant portions of the COB registry provided by the system to identify health plans having various responsibilities for paying for healthcare services provided to members covered by two or more health plans. The system may provide relevant portions of the COB registry prior to payments being made by health plans, thereby allowing upfront indications of which health plan should be used to pay for a given expense related to healthcare services obtained by a member who is covered by more than one health plan.

Figure 1:
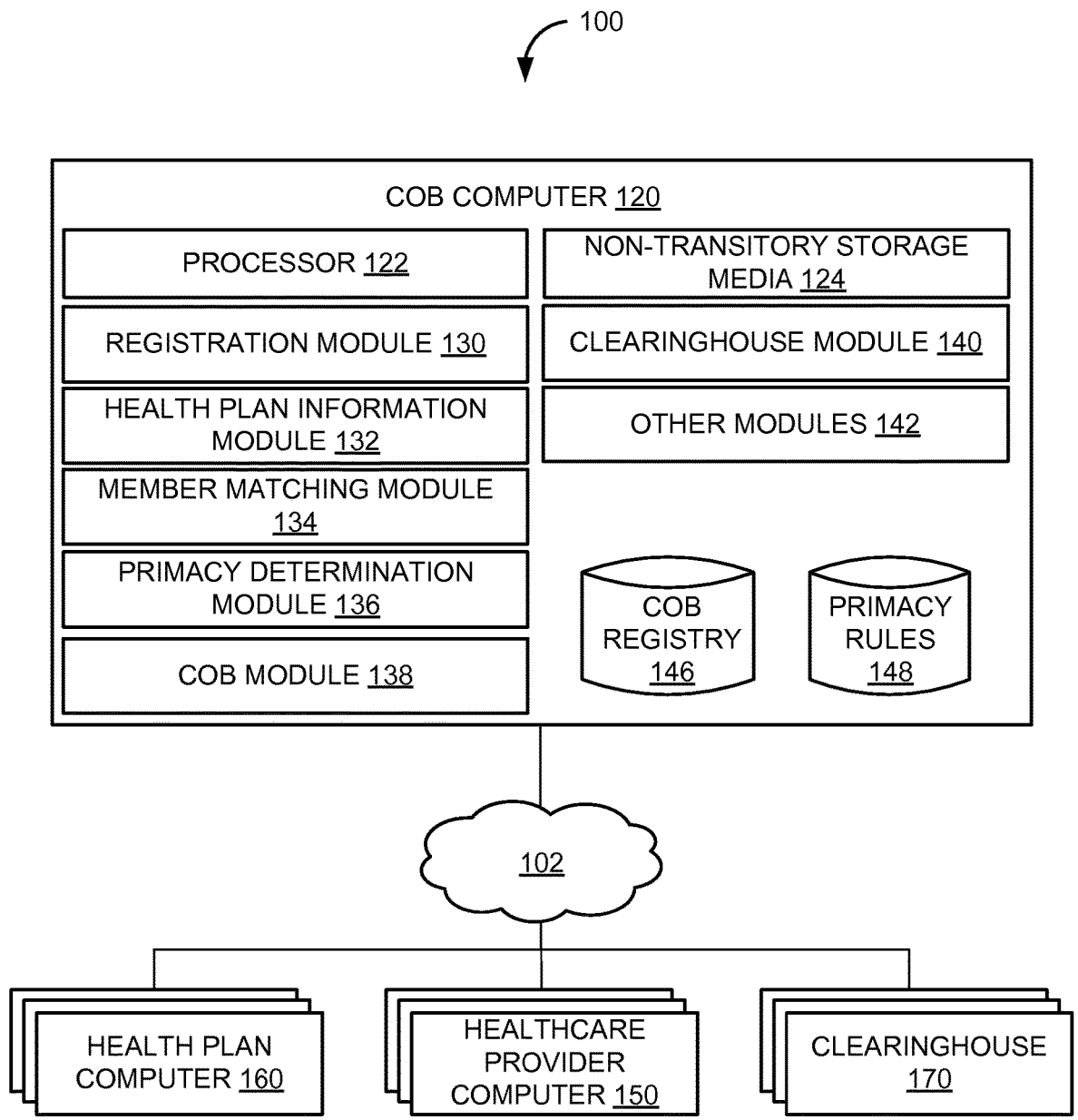
FIG. 1 illustrates a system configured to facilitate the coordination of benefits for a plurality of health plans that individually have at least some responsibility to pay for healthcare services received by members covered by more than one health plan, according to an aspect of the invention.

FIG. 1 illustrates an example of a system 100 configured to facilitate the coordination of benefits for a plurality of health plans that individually have at least some responsibility to pay for healthcare services received by members covered by more than one health plan, according to an aspect of the invention. System 100 may include a COB computer 120, one or more healthcare provider computers 150, one or more health plan computers 160, one or more clearinghouses 170, and/or other components.

According to an aspect of the invention, COB computer 120 may include one or more physical processors 122, non-transitory storage media 124, and/or other physical components. Non-transitory storage media 124 may be configured to store one or more computer program modules that program the one or more processors 122 to perform various functions described herein.

The one or more computer program modules may include, for example, a registration module 130, a health plan information module 132, a member matching module 134, a primacy determination module 136, a COB module 138, a clearinghouse module 140, and/or other modules 142.

According to an aspect of the invention, registration module 130 may be configured to register various users for interfacing with the system. The various users may include healthcare providers, health plans, members, and/or other entities that may access the information and functions provided by the system. For example, healthcare providers may register with the system in order to view health plans of their patients who are members of one or more health plans, health plans may register with the system in order to obtain primacy or other responsibility information for coordination of benefits for their members, and members/patients [not now but possibly in the future] may register with the system to be able to view and update their coverage information.

According to an aspect of the invention, health plan information module 132 may be configured to obtain health plan information from a plurality of health plans (e.g., via respective health plan computers 160). Health plan information may include sets of member information and sets of coverage information. A set of member information may include information that describes a member who is covered by a given health plan. For example, the member information may include a name, a gender, an address, and/or other information that describes the member. A set of coverage information may include information that describes a health plan, which is provided by the given health plan, that covers the member. The coverage information may include a name of the health plan, a health plan identifier that identifies the health plan, coverage information that indicates coverage provided by the health plan, primacy rules, and/or other information that describes the health plan.

According to an aspect of the invention, health plan information module 132 may be configured to obtain at least some of a set of member information and/or set of coverage information related to a member from healthcare providers (e.g., via respective healthcare provider computers 150), members (via respective member devices not illustrated in FIG. 1), and/or other sources.

A particular member may be covered by two or more health plans provided by respective health plans that individually may be unaware of coverage provided by other health plans of other health plans. For example, a first health plan may provide first health plan information and a second health plan may provide second health plan information. In the foregoing example, the first health plan information and the second health plan information may refer to a particular member without cross-referencing each other.

As such, according to an aspect of the invention, member matching module 134 may be configured to determine that the first health plan information and the second information correspond to the particular member. Member matching module 134 may make the determination based on matching identifying information contained in the first and second health plan information. The matches may be exact matches or inexact matches. For example, member matching module 134 may exactly match a member name ("John Doe") obtained from a first set of member information from a first health plan with a member name ("John Doe") obtained from a second set of member information from a second health plan. On the other hand, member matching module 134 may inexactly match a member name ("John Doe") of the first member information with a member name ("Jojn Doe") of the second member information. In these instances, member matching module 134 may account for typographical or other spelling errors using conventional matching/parsing techniques. Member matching module 134 may use other identifying information and/or combinations of identifying information as well. In some implementations, member matching module 134 may associate different individuals. For example, member matching module may determine that a first individual is a dependent of second individual, who may be covered by a health plan. Such matching may be based on, for example, a common last name, a common residence address, an explicit association, and/or other information that may indicate dependency or other relationship between two individuals.

According to an aspect of the invention, primacy determination module 136 may be configured to determine primacy information that identifies primary, secondary, and/or other payment responsibilities. For example, the primacy information may identify one or more health plans having primary responsibility to pay for the healthcare services received by a covered member and one or more health plans having secondary or other payment responsibilities to pay for the healthcare services. Primacy determination module 136 may determine the primacy information based on one or more primacy rules (illustrated in FIG. 1 as a database of primacy rules 148) that specify primary, secondary, and/or other payment responsibilities. The primacy rules 148 may be derived from or otherwise be included in the health plan information, governmental regulations (such as federal or local laws, regulations, etc.), and/or other source that may include the primacy rules. For example, a primacy rule may indicate that for whichever health plan covered a member for a longer period of time has primary responsibility.

According to an aspect of the invention, COB module 138 may be configured to generate a COB registry 146 for storing health plan information related to one or more health plans that cover a given member, primacy information, and/or other information related the coordination of benefits. In this manner, a given member that is covered by more than one health plan may be identified and information related to the health plans that cover the given member may be stored in association with information that identifies the given member. COB registry 146 may therefore serve as a central repository that stores an association of a given member with health plan information related to one or more health plans that cover the given member.

According to an aspect of the invention, COB module 138 may generate one or more COB records that indicate that the given member is covered by two or more health plans. For example, the one or more records may include a member identifier that identifies the given member, at least some of the coverage information from the two or more health plans, and/or other information related to the member, health plan, or health plan. The member identifier may be system-generated to represent the given member and/or may use member information (e.g., a name of the member) obtained from the two or more health plans.

The one or more COB records may be configured in various ways to enable an association between the member identifier and a first set of health plan information for a first health plan that covers the given member and a second set of health plan information for a second health plan that covers the given member.

For example, in one configuration, the member identifier may serve as a link between the health plan information (e.g., coverage information) of the two or more health plans. In this configuration, the first and second sets of health plan information (or at least portions thereof) may be stored in respective records that are linked with the member identifier such that the one or more COB records associates the member identifier and first and second sets of health plan information. In this manner, a member who is covered by two or more health plans may be associated with the two or more health plans.

In another configuration, a single record may be generated based on a combination of the member identifier and the first and second sets of health plan information (or at least portions thereof) such that the single record is used to associate the member identifier and the first and second sets of health plan information.

Other configurations of COB records may be used as well. Whichever configuration or combination of configurations of the one or more COB records is used, COB module 138 may store the COB records in COB registry 146.

According to an aspect of the invention, COB module 138 may provide at least a portion of COB registry 146 to various recipients such as health plans, healthcare providers, members, and/or other relevant entities. Information from COB registry 146 may be provided in various ways such as batch processing new or updated information to various recipients, providing the information on-demand responsive to a request for the information, and/or in other ways.

According to an aspect of the invention, COB module 138 may be configured to provide relevant portions of COB registry 146 to recipients. A portion of COB registry 146 may be relevant to the recipient when the information contained therein relates to the recipient. For example, a portion (e.g., one or more COB records) of COB registry 146 may be relevant to health plan when the portion relates to a member who is covered by the health plan. Such portion may include the health plan information of the health plan that covers the member and is provided by the health plan as well as health plan information of other health plans that also cover the member and are provided by other health plans. A portion of COB registry 146 may be relevant to a healthcare provider when the portion relates to patient of the healthcare provider. As such, different recipients may receive different relevant portions of COB registry 146.

According to an aspect of the invention, COB module 138 in a format that enables the health plans or other recipients to generate local copies of the relevant portions (e.g., records that pertain to that recipient) of the COB registry. The format may include bulk copy formats, XML formats, and/or other formats that enable others to generate local copies of relevant portions of the COB registry and/or otherwise consume the information. Because COB module 138 may provide different recipients with different relevant portions of COB registry 146, different recipients may therefore create different local copies of the COB registry or portions thereof.

These local copies may be periodically updated as new or updated relevant information is made available. Such updates or new information may include changed coverage, dropped health plan (e.g., no longer covered by a particular health plan), added health plan (e.g., newly covered by a health plan), and/or other new or updated information. In this manner, health plans or others may refer to their own local COB registries having updated information when making a determination of whether and/or how much to pay for a healthcare service received by a covered member.

According to an aspect of the invention, COB module 138 may be configured to provide relevant portions on-demand. COB module 138 may receive an information request from a recipient. The information request may identify a health plan, a member, and/or other information for which the recipient would like information from COB registry 146. Responsive to the request, COB module 138 may query COB registry 146 and provide information that satisfies the request.

According to an aspect of the invention, information from COB registry 146 may facilitate request and response messages, such as 270/271 messaging used in conventional eligibility, coverage or benefit inquiry (270) messages conventional eligibility, coverage or benefit response (271) messages. The 270 messages and/or the 271 messages may include information that is compatible with COB registry 146.

According to an aspect of the invention, clearinghouse module 138 may facilitate the inquiry and response. For example, clearinghouse module 138 may receive a message such as a 270 message (e.g., from a healthcare provider) for inquiring eligibility, coverage or benefit information for a given member. The 270 message may include information that is compatible with COB registry 146. For example, the 270 message may include a member identifier from COB registry. Clearinghouse module 138 may forward the 270 message to a clearinghouse 170, which forwards the request to an appropriate provider, which may generate a 271 response that based on relevant portions (e.g., records pertaining to members) of COB registry 146. The 271 response may be provided to the requester, which may proceed with billing the appropriate health plans based on the 270/271 messaging. Other types of messaging other than 270/271 messaging may be used to facilitate inquiry and responses using COB registry 146 as well.

The components illustrated in FIG. 1 may be communicably coupled to one another via various communication links such as network 102. Network 102 may include wired or wireless connections. In some aspects of the invention, network 102 may include any one or more of, for instance, the Internet, an intranet, a PAN (Personal Area Network), a LAN (Local Area Network), a WAN (Wide Area Network), a SAN (Storage Area Network), a MAN (Metropolitan Area Network), a wireless network, a cellular communications network, a Public Switched Telephone Network, and/or other network.

The databases (e.g., databases 146 and 148 and other databases described herein) described herein may be, include, or interface to, for example, an Oracle™ relational database sold commercially by Oracle Corporation. Other databases, such as Informix™, DB2 (Database 2) or other data storage, including file-based, or query formats, platforms, or resources such as OLAP (On Line Analytical Processing), SQL (Standard Query Language), a SAN (storage area network), Microsoft Access™ or others may also be used, incorporated, or accessed. The database may comprise one or more such databases that reside in one or more physical devices and in one or more physical locations. The database may store a plurality of types of data and/or files and associated data or file descriptions, administrative information, or any other data.

Those having skill in the art will recognize that healthcare provider computer 150, health plan computer 160, and clearinghouse 170 may each comprise one or more physical processors, one or more interfaces (to various peripheral devices or components), non-transitory storage media, and/or other components coupled via a bus. The non-transitory storage media (including non-transitory storage media 124 and those not illustrated in FIG. 1) may comprise random access memory (RAM), read only memory (ROM), or other memory. The memory may store computer-executable instructions to be executed by the processor as well as data that may be manipulated by the processor. The storage media may comprise floppy disks, hard disks, optical disks, tapes, or other storage media for storing computer-executable instructions and/or data.

The various modules described herein are exemplary only. Other configurations and numbers of modules may be used, as well using non-modular approaches so long as the one or more physical processors are programmed to perform the functions described herein.

Figure 2:
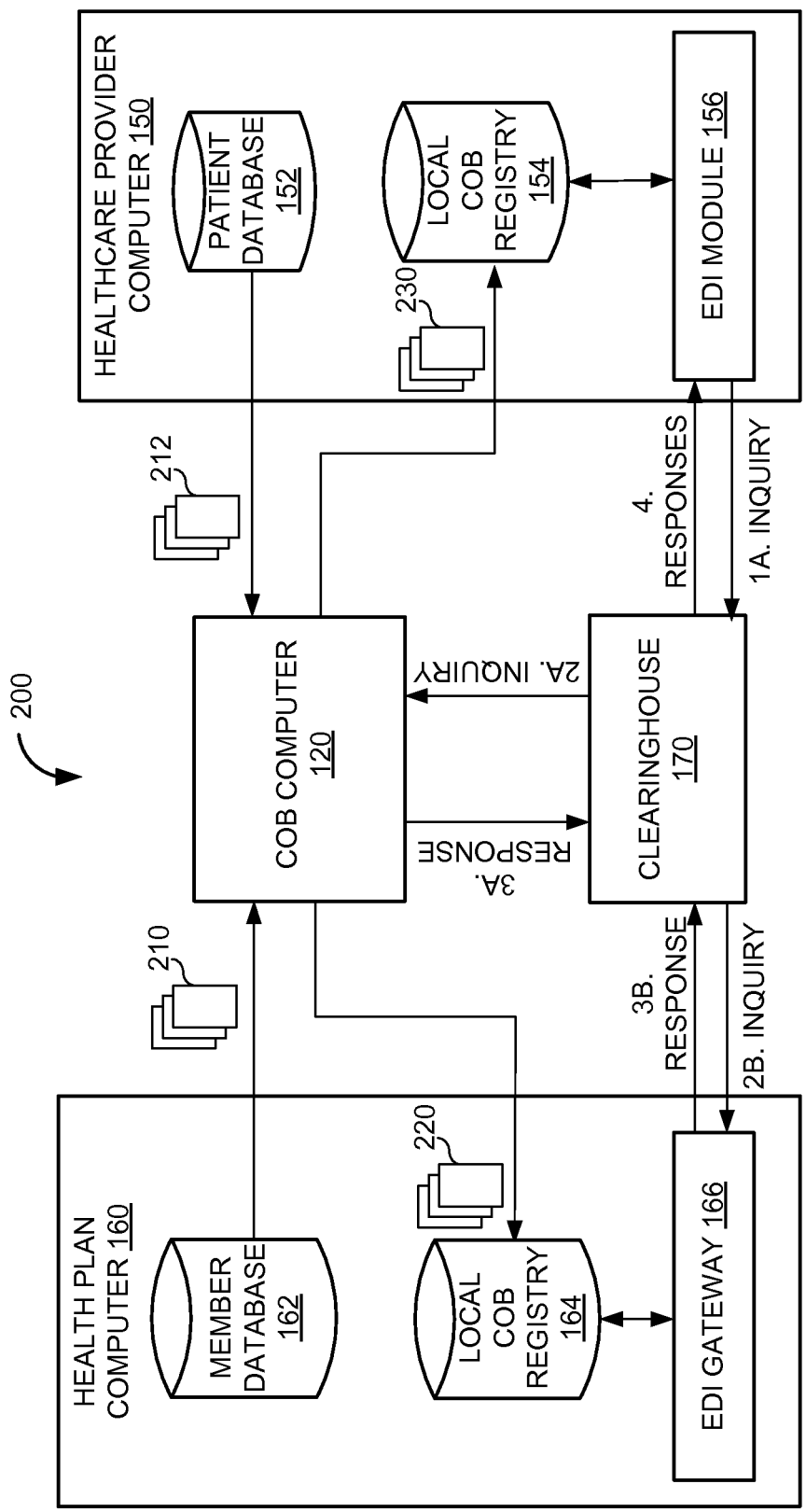
FIG. 2 illustrates an example of a data flow diagram for components of a system configured to facilitate the coordination of benefits for a plurality of health plans, according to an aspect of the invention.

FIG. 2 illustrates an example of a data flow diagram 200 for components of a system configured to facilitate the coordination of benefits for a plurality of health plans, according to an aspect of the invention.

According to an aspect of the invention, health plan computer 160 may include a member database 162, a local COB registry 164, an Electronic Data Interchange ("EDI") gateway 166, and/or other components. Member database 162 may include limited information related to members covered by the health plans provided by a health plan, which may include an entity that operates/controls health plan computer 160. The information related to members may include identifications of the members, coverage information for health plans that cover the members (e.g., health insurance policy information for a health insurance policy of a given member), and/or other information. Local COB registry 164 may include a local copy of information provided by COB computer 120. EDI gateway 166 may facilitate responses to inquiries made to the health plan. Such inquiries may be related to coverage information, billing information, and/or other inquiries to obtain information from the health plan.

According to an aspect of the invention, healthcare provider computer 150 may include a patient database 152, a local COB registry 154, an EDI module 156, and/or other components. Patient database 152 may include information related to patients treated by a healthcare provider, which may include an entity that operates/control healthcare provider computer 150. The information related to patients may include identifications of the patients (which may be the same as a member identification when both a health plan and a healthcare provider use the same identifier to identify patients and members or may be different than a member identification when the health plan uses a different identification than the healthcare provider). The information related to the patient may include health plan information such as coverage information provided from the patient to the healthcare provider.

By way of example only, in operation, COB computer 120 may facilitate various data flows illustrated with respect to FIG. 2. COB computer 120 may receive health plan information 210 from health plan computer 160 via a communication mechanism such as via a membership file, web services, and/or other communication mechanism. Health plan information may relate to all or a portion of the members stored in member database 162. Such health plan information may include, for each member whose information is communicated by health plan information 210, a set of member information and a set of coverage information. Health plan information may include different sets of member information that individually relate to different members and different sets of coverage information that individually relate to different members. A set of member information and a set of coverage information need not be separate, as they may be included in a single or multiple records.

COB computer 120 may perform member matching as described above with respect to FIG. 1 and generate one or more COB records for storage in COB registry 146 (illustrated in FIG. 1). Either upon request and/or other process such as a batched process or responsive to events such as an update to the information in COB registry 146, COB computer 120 may provide relevant portions 220 of the COB registry back to health plan computer 160, which may generate a local COB registry 164 based on the relevant portions. An exemplary illustration of relevant portions of COB registry 146 provided for various local registries is provided in FIG. 3.

Likewise, COB computer 120 may receive patient information 212 from healthcare provider computer 150 via a communication mechanism such as via a membership file, web services, and/or other communication mechanism. The patient information may relate to all or a portion of the patients stored in patient database 152. Such patient information may include an identification of the patient, one or more patient demographics (e.g., age, gender, etc.), health plan coverage information, and/or other information related to the patients.

Either upon request and/or other process such as a batched process or responsive to events such as an update to the information in COB registry 146, COB computer 120 may obtain a relevant portion 230 of COB registry 146 for a healthcare service provider and provider the relevant portion to healthcare provider computer 150. For example, relevant portion 230 may include health plan information for all or a portion of the patients of the healthcare service provider. Healthcare provider computer 150 may generate local COB registry 154 based on relevant portion 230.

According to an aspect of the invention, the provision of information from COB registry 146 may facilitate various inquiry/response messaging, such as 270/271 messaging conventionally used to make inquiries and provide responses to the inquiries. For example, because different parties may use the same or similar types/formats of information (such as member identifications, health plan identifications, associations between the member identifications and the health plan identifications, and/or other information facilitated by COB registry 146), the content of inquiry/response messaging may be made uniform and understandable by the different parties. An inquiry/response message may relate to health plan information, billing information (e.g., specific billing inquiries to pay a specific amount related to provision of healthcare services, general billing inquiries such as primacy information, etc.), and/or other information that may be conveyed using information from COB registry 146. An inquiry/response may be made between various parties such as between health plans, healthcare providers, the COB computer 120, clearinghouses, and/or other parties that wish to inquire/respond to inquiries related to members and/or health plans.

Inquiry/response messaging may be made between and/or facilitated by various components. For example, EDI module 156 may generate inquiries related to health plan coverage of patients and receive responses. EDI module 156 may communicate the inquiries to COB computer 120 and receive responses to the inquiries back from COB computer 120. Responsive to the inquiries, COB computer 120 may use clearinghouse 170, which provides the inquiries to EDI gateway 166. EDI module 156 may provide the inquiries to clearinghouse 170 as well. EDI gateway 166 may consult with local COB registry 164 in order to determine a response to the inquiry. For example, the response may include coverage eligibility information that is determined at health plan computer 160 based on health plan information stored at local COB registry 164.

The response may be provided by EDI gateway 166 to clearinghouse 170, which provides the response back to EDI module 156 either directly or via COB computer 120, depending on which component made the inquiry to clearinghouse 170. Although not illustrated, in one aspect, COB computer may communicate inquiries to and receive responses back from EDI gateway 166 directly. Although also not illustrated, various inquiries/responses may be communicated to and from different health plan computers 160 using similar data flows illustrated in FIG. 2 (e.g., direct communication, mediated by clearinghouse 170, mediated by COB computer 120, etc.).

Discovery of Additional Health Plans that Cover a Member

In some implementations, COB computer 120 facilitates discovery of one or more additional health plans that cover a member. For example, a patient may inform a healthcare service provider that the patient is covered by a first health plan. At operation 1A, the healthcare service provider may send an inquiry message (whether 270/271 messages or not) to a clearinghouse 170 to inquire about eligibility and/or payment. At one or more operations 2A and 2B, clearinghouse 170 may forward the inquiry to both the first health plan (e.g., health plan computer 160) and COB computer 170. The first health plan may respond with eligibility or other information in operation 3B. The COB computer 120 may respond that a second health plan also provides coverage for the patient and optionally may also include primacy and/or coverage information if available in an operation 3A. The clearinghouse 170 may forward both responses to the healthcare service provider computer 150 in an operation 4, thereby informing the provider that the patient is also covered by the second health plan. In some implementations, COB computer 120 include a clearinghouse 170 or clearinghouse functionality. In other implementations, clearinghouse 170 may be separate from COB computer 120 and/or operated by a different entity than the entity that operates COB computer 120.

The various data flows illustrated in FIG. 2 provide various channels by which health plan information, and inquiries/responses related to the health plan information may be communicated between different parties. The various channels of information may be facilitated through the creation and provision of information from COB registry 146.

Figure 3:
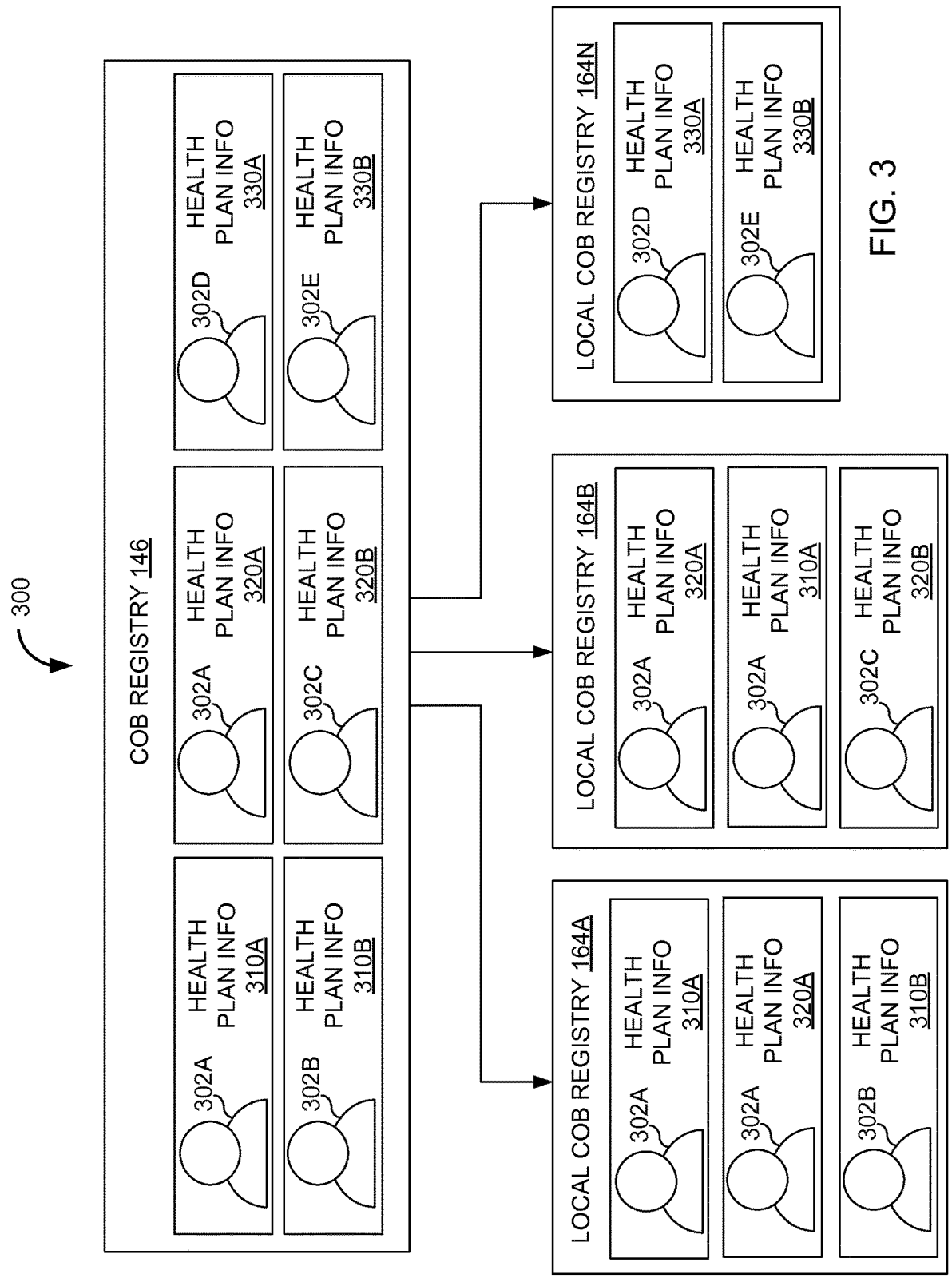
FIG. 3 is a block diagram illustrating an example of providing relevant portions of a central coordination of benefits registry for creation or update of a local coordination of benefits registry, according to an aspect of the invention.

FIG. 3 is a block diagram 300 illustrating an example of providing relevant portions of a central coordination of benefits registry for creation or update of a local coordination of benefits registry, according to an aspect of the invention. COB registry 146 may be configured as a central registry that may provide relevant portions of information stored therein for creation or update of local registries 164 (illustrated in FIG. 3 as local registries 164A, 164B, . . . , 164N). Local registries 164 may be stored at a respective health plan computer and/or other respective computer operated/controlled by other entities.

As illustrated, COB registry 146 stores information related to a plurality of members 302 (illustrated in FIG. 3 as members 302A, 302B, 302C, 302D, 302E). Other numbers of members 302 may be stored as well. COB registry 146 may store associations between identities of individual members 302 and respective health plan information (illustrated in FIG. 3 as health plan info 310A, 310B, 320A, 320B, 330A, and 330B). Individual health plan information may describe a health plan that covers a member 302. Some members 302 may be covered by more than one health plan. For example, member 302A may be covered by a health plan described by health plan info 310A and also by another health plan described by health plan info 320A.

Different local COB registries 164 may be provided with different relevant portions of COB registry 146. The relevant portions may be determined based on members covered by a health plan. For example, a first health plan may maintain local COB registry 164 and may provide health plans described by health plan info 310A and 310B for members 302A and 302B. A second health plan may maintain local COB registry 164B and provide health plans described by health plan info 320A and 320B for members 302A and 302C. A third health plan may maintain local COB registry 164N and provide health plans described by health plan info 330A and 330B for members 302D and 302E.

As illustrated, health plan info 310A, and health plan info 310B may be a relevant portion to provide for local COB registry 164A because they involve health plans provided to members 302A and 302B by the first health plan. Additionally, health plan info 320A may be a relevant portion for local COB registry 164A because health plan info 320A describes a health plan provided by the second health plan for member 302A. Thus, the first health plan may be provided with information related to one of its members that is covered by another health plan, which may be provided by another health plan.

Similarly, health plan info 320A, and health plan info 320B may be a relevant portion to provide for local COB registry 164B because they involve health plans provided to members 302A and 302C by the second health plan. Additionally, health plan info 310A may be a relevant portion for local COB registry 164B because health plan info 310A describes a health plan provided by the first health plan for member 302A. Thus, the second health plan may be provided with information related to one of its members that is covered by another health plan, which may be provided by another health plan.

On the other hand, only health plan info 330A, and health plan info 330B may be a relevant portion to provide for local COB registry 164N because the third health plan does cover any members that are also covered by another health plan. Thus, health plan info 310A and 320A is not relevant for the third health plan who maintains/controls local COB registry 164.

The provisioning of relevant portions of COB registry 146 described with respect to FIG. 3 may be performed by one or more components illustrated in FIG. 1 or 2 described above.

Figure 4:
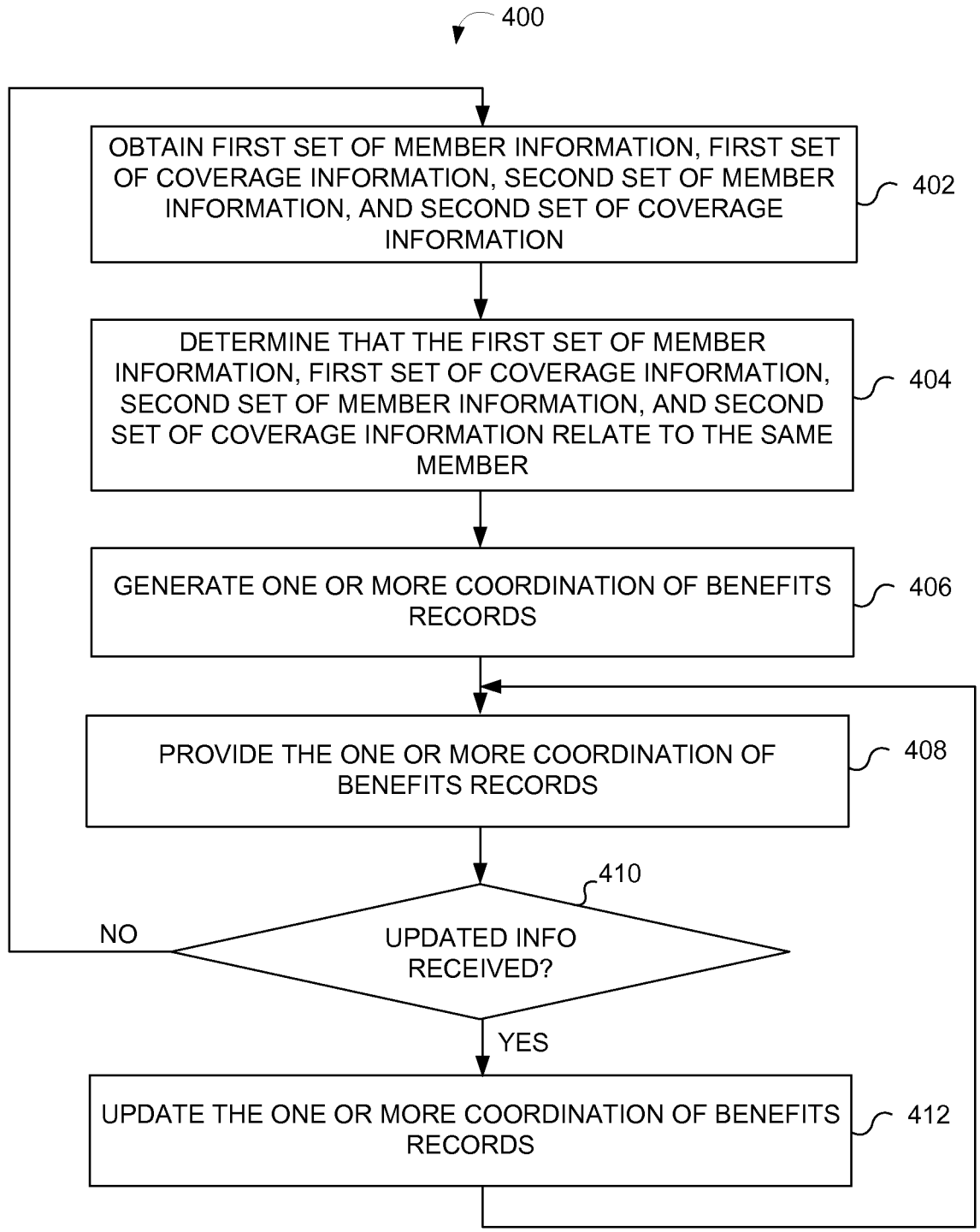
FIG. 4 illustrates an example of a process for facilitating the coordination of benefits for a plurality of health plans that individually have at least some responsibility to pay for healthcare services received by members covered by more than one health plan, according to an aspect of the invention.

FIG. 4 illustrates an example of a process 400 for facilitating the coordination of benefits for a plurality of health plans that individually have at least some responsibility to pay for healthcare services received by members covered by more than one health plan, according to an aspect of the invention. The various processing operations depicted in the flowchart of FIG. 4 are described in greater detail herein. The described operations may be accomplished using some or all of the system components described in detail above.

According to an aspect of the invention, various operations may be performed in different sequences. In other implementations, additional operations may be performed along with some or all of the operations shown in FIG. 4, or some operations may be omitted. In yet other implementations, one or more operations may be performed simultaneously. Accordingly, the operations as illustrated (and described in greater detail below) are exemplary in nature and, as such, should not be viewed as limiting.

In an operation 402, a first set of member information that describes a member covered by a first health plan, a first set of coverage information that describes the first health plan in relation to the member covered by the first health plan, a second set of member information that describes a member covered by a second health plan, and a second set of coverage information that describes the second health plan in relation to the member covered by the second health plan may be obtained. The information described in operation 402 may be obtained (e.g., passively received, actively retrieved, etc.) from health plans, healthcare providers, members, and/or others who may provide such information.

In an operation 404, the first set of member information, the first set of coverage information, the second set of member information, and the second set of coverage information may be determined to relate to a particular member that is covered by both the first health plan and the second health plan based on the first set of member information and the second set of member information. For example, operation 404 may include member matching based on the first set of member information and the second set of member information. The member matching may be exact or inexact matches, as would be appreciated by those having skill in the art.

In an operation 406, one or more coordination of benefits records may be generated. The one or more coordination of benefits records may indicate that the particular member is covered by both the first health plan and the second health plan and may include at least a portion of the first set of coverage information, at least a portion of the second set of coverage information, and a member identifier that identifies the particular member.

In an operation 408, the one or more coordination of benefits records may be provided. For example, the one or more coordination of benefits records may be provided to a health plan for determining whether and/or how much to pay for a healthcare service received by one of its members. The health plan may determine whether other health plans have primary, secondary, and/or other responsibility to pay for the healthcare service. The one or more coordination of benefits records may be provided to a healthcare provider for determining whether and/or how much to request payment from a particular health plan. The one or more coordination of benefits records may be provided to other recipients and/or for other purposes as well.

In an operation 410, a determination of whether updated information has been received may be made. Updated information may include new information or updated information related to the first set of member information, the first set of coverage information, the second set of member information, and/or the second set of coverage information.

If updates have been received, the one or more coordination of benefits records may be updated (such as in COB registry 146 illustrated in FIG. 1) in an operation 412. Processing may the return to operation 408, where the one or more coordination of benefits records, which has been updated, may be provided.

Figure 5:
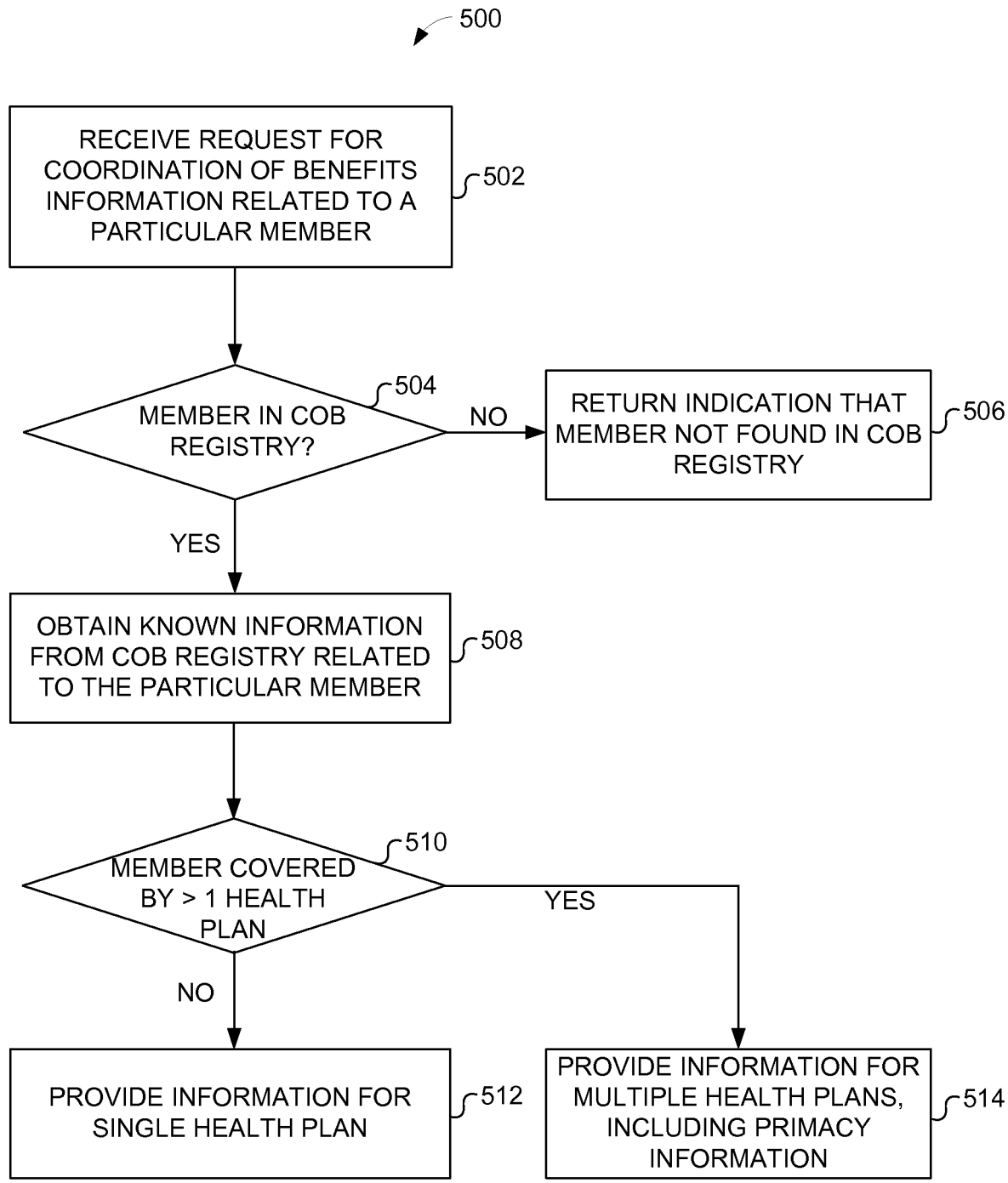
FIG. 5 illustrates an example of a process for providing coordination of benefits information responsive to an inquiry related to coverage information for a member of one or more health plans, according to an aspect of the invention.

FIG. 5 illustrates an example of a process 500 for providing coordination of benefits information responsive to an inquiry related to coverage information for a member of one or more health plans, according to an aspect of the invention. The various processing operations depicted in the flowchart of FIG. 5 are described in greater detail herein. The described operations may be accomplished using some or all of the system components described in detail above.

According to an aspect of the invention, various operations may be performed in different sequences. In other implementations, additional operations may be performed along with some or all of the operations shown in FIG. 5, or some operations may be omitted. In yet other implementations, one or more operations may be performed simultaneously. Accordingly, the operations as illustrated (and described in greater detail below) are exemplary in nature and, as such, should not be viewed as limiting.

In an operation 502, a request for coordination of benefits information related to a particular member may be received. For example, the request may include a member identifier such as a name, an identifier that was assigned by the system, an identifier that was assigned by one or more health plans, and/or other identifier.

In an operation 504, a determination of whether the particular member is stored in the COB registry may be made. If information related to the particular member is not stored in the COB registry, an indication that the member was not found in the COB registry may be returned in an operation 506. On the other hand, if information related to the particular member is stored in the COB registry, known information about the particular member may be obtained in an operation 508. The known information may be included in one or more COB records and may relate to one or more health plans that cover the particular member.

In an operation 510, a determination of whether the particular member is covered by more than one health plan may be made. On the other hand, if the particular member is covered by more than one health plan, information related to each health plan that covers the particular member may be provided in an operation 514. The information related to each health plan may include primacy information that identifies primary, secondary, and/or other payment responsibilities for at least one of the health plans.

Figure 6:
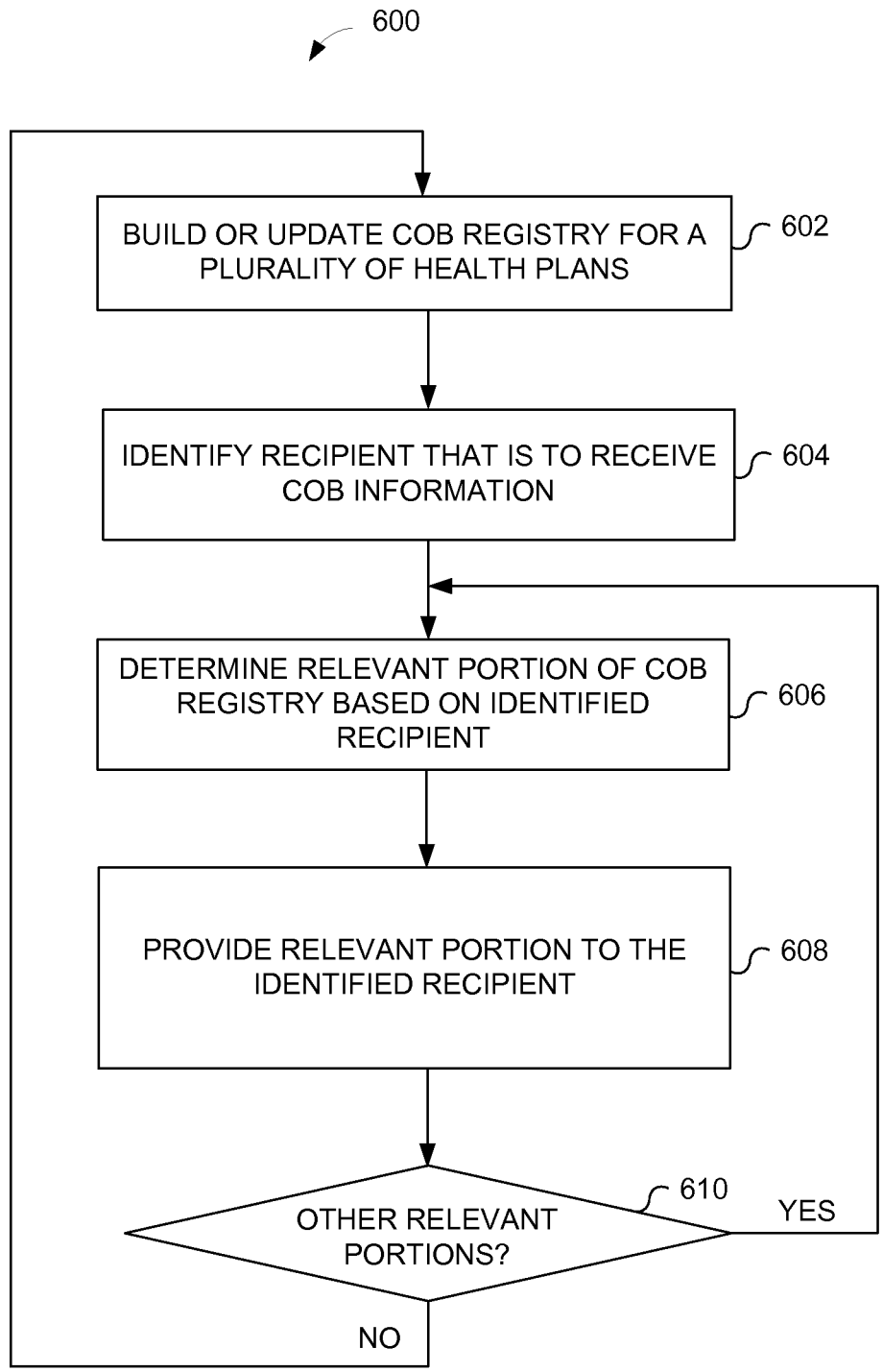
FIG. 6 illustrates an example of a process for providing coordination of benefits information for storage by a health plan in a local coordination of benefits registry, according to an aspect of the invention.

FIG. 6 illustrates an example of a process 600 for providing coordination of benefits information for storage in a local coordination of benefit registry, according to an aspect of the invention. The various processing operations depicted in the flowchart of FIG. 6 are described in greater detail herein. The described operations may be accomplished using some or all of the system components described in detail above.

According to an aspect of the invention, various operations may be performed in different sequences. In other implementations, additional operations may be performed along with some or all of the operations shown in FIG. 6, or some operations may be omitted. In yet other implementations, one or more operations may be performed simultaneously. Accordingly, the operations as illustrated (and described in greater detail below) are exemplary in nature and, as such, should not be viewed as limiting.

In an operation 602, a COB registry may be built or updated. The COB registry may be based on health plan information from a plurality of health plans. Individual health plan information may relate to a member covered by an individual health plan provided by a health plan. Thus, the COB registry may store health plan information related to a plurality of members who may individually be covered by more than one health plan.

In an operation 604, recipient that is to receive COB information may be identified. For example, process 600 may be responsive to a request by a recipient for the COB information, a batch process that provides the COB information for pre-identified recipients on a periodic basis, and/or responsive to other types of request for the COB information.

In an operation 606, relevant portions of the COB registry may be determined based on the identified recipient. For example, if the recipient is a health plan seeking information related to its members, the relevant portions may include portions of the COB registry that relate to members of the health plan. In this example, relevant portions may include health plan information of other health plans that cover the member and are provided by other health plans. On the other hand, if the recipient is a healthcare provider, the relevant portions may relate to patients of the healthcare provider.

In an operation 608, the relevant portions of the COB registry may be provided via a graphical user interface, electronic mail, FTP, XFTP, XML, and/or other communication channel, which may be encrypted or otherwise secured as necessary.

In an operation 610, a determination of whether there are other relevant portions may be made. If other relevant portions remain in the COB registry for the recipient, processing may return to operation 606, where the relevant portion is determined. On the other hand, if no other relevant portions remain in the COB registry for the recipient, processing may return to operation 602, wherein the COB registry may be updated.

Although described in the context of coordination of benefits for health plans, the systems and methods disclosed herein may be used in other contexts as well. For example, the COB registry may relate to various healthcare fields such as vision, dental, behavioral, other fields such as insurance subrogation such as for property/auto insurance, worker's compensation, and/or managing international responsibilities as related to different international regulations. Other aspects, uses and advantages of the invention will be apparent to those skilled in the art from consideration of the specification and practice of the invention disclosed herein. The specification should be considered exemplary only, and the scope of the invention is accordingly intended to be limited only by the following claims.

What is claimed is:

1. A computer-implemented method of managing a central coordination of benefits registry and sharing information with multiple local coordination of benefits registries to facilitate the coordination of benefits for multiple health plans that individually have at least some responsibility to pay for one or more medical expenses for healthcare services received by members covered by more than one health plan, the coordination of benefits being made prior to payment for the healthcare services, wherein the multiple local coordination of benefits registries are separate and remote from the central coordination of benefits registry and include at least a first local coordination of benefits registry associated with a first entity comprising coverage information for a first set of members associated with the first entity and a second local coordination of benefits registry associated with a second entity comprising coverage information for a second set of members associated with the second entity that is different from the first set of members, the method being implemented on a computer that includes one or more physical processors programmed with computer program instructions that, when executed by the one or more physical processors, program the computer to perform the method, the method comprising:

obtaining, by the one or more physical processors: (i) a first set of member information that describes a member covered by a first health plan; and (ii) a second set of member information that describes a member covered by a second health plan;

comparing, by the one or more physical processors, at least a portion of the first set of member information and at least a portion of the second set of member information;

determining, by the one or more physical processors, that the first set of member information and the second set of member information both relate to a first member that is covered by both the first health plan and the second health plan based on the comparison;

identifying, by the one or more physical processors, first coverage information that indicates a first responsibility of the first health plan to pay for at least a first portion of one or more medical expenses related to the first member based on the first set of member information, and second coverage information that indicates a second responsibility of the second health plan to pay for at least a second portion of the one or more medical expenses related to the first member based on the second set of member information;

generating, by the one or more physical processors, prior to payment of the one or more medical expenses by the first health plan or the second health plan, one or more coordination of benefits records that indicate that the first member is covered by both the first health plan and the second health plan based on the determination, wherein the one or more coordination of benefits records have a common data structure comprising (i)

the first coverage information, (ii) the second coverage information, and (iii) a member identifier that identifies the first member;

updating, by the one or physical processors, a central coordination of benefits registry maintained by the one or more physical processors based on the one or more coordination of benefits records, the central coordination of benefits registry storing coverage information on a per member basis, the coverage information including information indicating one or more health plans related to individual members and how medical expenses for the individual members are to be apportioned among the one or more health plans, wherein the central coordination of benefits registry includes coordination of benefits records having the common data structure for individual members that are covered by two or more health plans;

identifying, by the one or physical processors, a first set of information from the central coordination of benefits registry for a first set of members associated with the first entity and a second set of information from the central coordination of benefits registry for a second set of members associated with the second entity;

transmitting, by the one or more physical processors, the first set of information to a device of the first entity to facilitate updating the first local coordination of benefits registry; and transmitting, by the one or more physical processors, the second set of information to a device of the second entity to facilitate updating the second local coordination of benefits registry.

2. The computer-implemented method of claim 1, wherein the first set of member information comprises first identifying information used to identify the member covered by the first health plan and the second set of member information comprises second identifying information used to identify the member covered by the second health plan and wherein determining that the first set of member information and the second set of member information relate to the first member based on the comparison comprises:

identifying, by the one or more physical processors, a match between the first identifying information and the second identifying information.

3. The method of claim 2, wherein the first identifying information comprises a first name and the second identifying information comprises a second name, and wherein identifying a match between the first identifying information and the second identifying information comprises:

comparing, by the one or more physical processors, the first name with the second name;

determining, by the one or more physical processors, an inexact, but at least partial, match between the first name and second name;

comparing, by the one or more physical processors, a first portion of the first set of member information other than the first name with a second portion of the second set of member information other than the second name; and determining, by the one or more physical processors, that the first set of member information and the second set of member information relate to the first member based on the inexact, but at least partial match between the first name and the last name and the comparison of the first portion of the first set of member information other than the first name with the second portion of the second set of member information other than the second name, wherein the comparison of the first portion of the first set of member information other than the first name with the second portion of the second set of member information other than the second name is used to supplement the inexact, but at least partial, match between the first name and the second name.

4. The computer-implemented method of claim 1, wherein generating the one or more coordination of benefits records comprises:

obtaining, by the one or more physical processors, primacy information for the first member indicating how medical expenses are to be apportioned among the first health plan and the second health plan, wherein the primacy information dictates that the first health plan has a primary responsibility to pay for the one or more medical expenses and the second health plan has a secondary responsibility to pay for the one or more medical expenses, wherein the one or more coordination of benefits records further comprise the primacy information.

5. The computer-implemented method of claim 4, the method further comprising:

determining, by the one or more physical processors, that an update to the first coverage information has been received;

responsive to the determination that an update to the first coverage information has been received, updating, by the one or more physical processors, the one or more coordination of benefits records based on the update to the first coverage information; and causing, by the one or more physical processors, the updated one or more coordination of benefits records to be provided.

6. The method of claim 4, wherein the primacy information is determined based on one or more primacy rules for apportioning medical expenses, the method further comprising:

analyzing, by the one or more physical processors, the one or more primacy rules;

determining, by the one or more physical processors prior to payment of the one or more medical expenses, a first apportionment of the one or more medical expenses for which the first health plan is responsible to pay based on the analysis of the one or more primacy rules; and determining, by the one or more physical processors prior to payment of the one or more medical expenses, a second apportionment of the one or more medical expenses for which the second health plan is responsible to pay based on the analysis of the one or more primacy rules.

7. The computer-implemented method of claim 1, wherein the first entity comprises a first health plan provider of the first health plan and the second entity comprises a second health plan provider of the second health plan, the method further comprising:

identifying, by the one or more physical processors, the first set of information based on a first set of health plans that cover a given member of the first health plan to thereby identify other health plans that cover the given member of the first health plan; and identifying, by the one or more physical processors, the second set of information based on a second set of health plans that cover a given member of the second health plan to thereby identify other health plans that cover the given member of the second health plan.

8. The computer-implemented method of claim 1, the method further comprising:

determining, by the one or more physical processors, that an update to the first coverage information has been received;

responsive to the determination that an update to the first coverage information has been received, updating, by the one or more physical processors, the one or more coordination of benefits records based on the update to the first coverage information; and causing, by the one or more physical processors, the updated one or more coordination of benefits records to be provided.

9. The computer-implemented method of claim 1, wherein the first entity comprises a first health plan provider of the first health plan, the method further comprising:

formatting, by the one or more physical processors, the first set of information into a format that facilitates incorporation of the one or more coordination of benefits records into the first local coordination of benefits registry stored locally by the first health plan provider.

10. The computer-implemented method of claim 1, wherein the first entity comprises a first healthcare service provider, the method further comprising:

causing, by the one or more physical processors, the first set of information to be provided to a healthcare service provider computer of the first healthcare service provider responsive to a request from the healthcare service provider computer.

11. The computer-implemented method of claim 1, the method further comprising:

receiving, by the one or more physical processors, an inquiry request from a clearinghouse related to a second member;

obtaining, by the one or more physical processors, information indicating that the second member is covered by a second health plan; and causing, by the one or more physical processors, the information indicating the second member is covered by the second health plan to be provided to the clearinghouse responsive to the inquiry request.

12. The method of claim 1, wherein the first health plan is provided by a first health plan provider that is obligated to pay for the first portion of the one or more medical expenses through the first health plan and the second health plan is provided by a second health plan provider that is different from the second health plan provider and is obligated to pay for the second portion of the one or more medical expenses through the second health plan.

13. The method of claim 1, the method further comprising:

obtaining, by the one or more processors, pre-stored registration information that indicates the first recipient is a healthcare provider that has been previously registered to access the coordination of benefits registry, wherein identifying the first relevant portion comprises:

determining, by the one or more processors, that the first member is a patient of the healthcare provider;

determining, by the one or more processors, that the first coverage information and the second coverage information should be included in the first set of information based on the determination that the first member is a patient of the healthcare provider;

identifying, by the one or more processors, that a second member in the coordination of benefits registry is a patient of the healthcare provider;

identifying, by the one or more processors, at least third coverage information that indicates a third responsibility of a health plan to pay for one or more medical expenses related to the second member; and determining, by the one or more processors, that the third coverage information related to the second member should be included in the first set of information.

14. The method of claim 1, wherein the first recipient comprises a first health plan provider that provides the first health plan, the method further comprising:

obtaining, by the one or more processors, pre-stored registration information that indicates the first recipient is a health plan provider that has been previously registered to access the coordination of benefits registry, wherein identifying the first relevant portion comprises:

determining, by the one or more processors, that the first member is covered by the first health plan;

determining, by the one or more processors, the first coverage information and the second coverage information should be included in the first set of information based on the determination that the first member is covered by the first health plan;

identifying, by the one or more processors, a second member in the coordination of benefits registry that is covered by the first health plan;

identifying, by the one or more processors, at least third coverage information that indicates a third responsibility of the first health plan to pay for one or more medical expenses related to the second member; and determining, by the one or more processors, that the third coverage information should be included in the first set of information.

15. The method of claim 1, wherein the second set of information includes at least a portion of the first set of information such that the second entity is provided with information relevant to at least the first coverage information.

16. The method of claim 15, wherein the first set of information includes at least a portion of the second set of information such that the first entity is provided with information relevant to at least the second coverage information.

17. The computer-implemented method of claim 1, wherein the first entity comprises a first health plan provider of the first health plan and the second entity comprises a second health plan provider of the second health plan, wherein the first local coordination of benefits registry is stored and maintained locally at the first health plan provider, and wherein the second local coordination of benefits registry is stored and maintained locally at the second health plan provider.

18. A system of managing a central coordination of benefits registry and sharing information with multiple local coordination of benefits registries to facilitate the coordination of benefits for multiple health plans that individually have at least some responsibility to pay for one or more medical expenses for healthcare services received by members covered by more than one health plan, the coordination of benefits being made prior to payment for the healthcare services, wherein the multiple local coordination of benefits registries are separate and remote from the central coordination of benefits registry and include at least a first local coordination of benefits registry associated with a first entity comprising coverage information for a first set of members associated with the first entity and a second local coordination of benefits registry associated with a second entity comprising coverage information for a second set of members associated with the second entity that is different from the first set of members, the system comprising:
  a computer comprising one or more physical processors programmed with computer program instructions that, when executed by the one or more physical processors, program the computer to:
    obtain: (i) a first set of member information that describes a member covered by a first health plan; and (ii) a second set of member information that describes a member covered by a second health plan;
    compare at least a portion of the first set of member information and at least a portion of the second set of member information;
    determine that the first set of member information and the second set of member information relate to a first member that is covered by both the first health plan and the second health plan based on the comparison;
    identify first coverage information that indicates a first responsibility of the first health plan to pay for at least a first portion of one or more medical expenses related to the first member based on the first set of member information, and second coverage information that indicates a second responsibility of the second health plan to pay for at least a second portion of the one or more medical expenses related to the first member based on the second set of member information;
    generate, prior to payment of the one or more medical expenses by the first health plan or the second health plan, one or more coordination of benefits records that indicate that the first member is covered by both the first health plan and the second health plan based on the determination, wherein the one or more coordination of benefits records have a common data structure comprising (i) the first coverage information, (ii) the second coverage information, and (iii) a member identifier that identifies the first member;
    update a central coordination of benefits registry maintained by the one or more physical processors based on the one or more coordination of benefits records, the central coordination of benefits registry storing coverage information on a per member basis, the coverage information including information indicating one or more health plans related to individual members and how medical expenses for the individual members are to be apportioned among the one or more health plans, wherein the central coordination of benefits registry includes coordination of benefits records having the common data structure for individual members that are covered by two or more health plans;
    identify a first set of information from the central coordination of benefits registry for a first set of members associated with the first entity and a second set of information from the central coordination of benefits registry for a second set of members associated with the second entity;
    transmit the first set of information to a device of the first entity to facilitate updating the first local coordination of benefits registry; and
    transmit the second set of information to a device of the second entity to facilitate updating the second local coordination of benefits registry.

19. The system of claim 18, wherein the first set of member information comprises first identifying information used to identify the member covered by the first health plan and the second set of member information comprises second identifying information used to identify the member covered by the second health plan, and wherein to determine that the first set of member information and the second set of member information relate to the first member based on the comparison, the computer is further programmed to:
  identify a match between the first identifying information and the second identifying information.

20. The system of claim 18, wherein to generate the one or more coordination of benefits records, the computer is further programmed to:
  obtain primacy information for the first member indicating how medical expenses are to be apportioned among the first health plan and the second health plan, wherein the primacy information dictates that the first health plan has a primary responsibility to pay for the one or more medical expenses and the second health plan has a secondary responsibility to pay for the one or more medical expenses, wherein the one or more coordination of benefits records further comprise the primacy information.

21. The system of claim 20, wherein the computer is further programmed to:
  determine that an update to the first coverage information has been received;
  responsive to the determination that an update to the first coverage information has been received, update the one or more coordination of benefits records based on the update to the first coverage information; and
  cause the updated one or more coordination of benefits records to be provided.

22. The system of claim 18, wherein the first entity comprises a first health plan provider of the first health plan and the second entity comprises a second health plan provider of the second health plan, wherein the computer is further programmed to:
  identify the first set of information based on a first set of health plans that cover a given member of the first health plan to thereby identify other health plans that cover the given member of the first health plan; and
  identify the second set of information based on a second set of health plans that cover a given member of the second health plan to thereby identify other health plans that cover the given member of the second health plan.

23. The system of claim 18, wherein the computer is further programmed to:
  determine that an update to the first coverage information has been received;
  responsive to the determination that an update to the first coverage information has been received, update the one or more coordination of benefits records based on the update to the first coverage information; and
  cause the updated one or more coordination of benefits records to be provided.

24. The system of claim 18, wherein the first entity comprises a first health plan provider of the first health plan, and wherein the computer is further programmed to:
  format the first set of information into a format that facilitates incorporation of the one or more coordination of benefits records into the first local coordination of benefits registry stored locally by the first health plan provider.

25. The system of claim 18, wherein the first entity comprises a first healthcare service provider, wherein the computer is further programmed to:
  cause the first set of information to be provided to a healthcare service provider computer of the first healthcare service provider responsive to a request from the healthcare service provider computer.

26. The system of claim 18, wherein the computer is further programmed to:
receive an inquiry request from a clearinghouse related to a second member;
obtain information indicating that the second member is covered by a second health plan; and
cause the information indicating the second member is covered by the second health plan to be provided to the clearinghouse responsive to the inquiry request.

27. The system of claim 18, wherein the first entity comprises a first healthcare service provider and the second entity comprises a second healthcare service provider,
wherein the first local coordination of benefits registry is stored and maintained locally at the first healthcare service provider, and
wherein the second local coordination of benefits registry is stored and maintained locally at the second healthcare service provider.

28. A non-transitory computer readable medium comprising computer program instructions for managing a central coordination of benefits registry and sharing information with multiple local coordination of benefits registries to facilitate the coordination of benefits for multiple health plans that individually have at least some responsibility to pay for one or more medical expenses for healthcare services received by members covered by more than one health plan, the coordination of benefits being made prior to payment for the healthcare services, wherein the multiple local coordination of benefits registries are separate and remote from the central coordination of benefits registry and include at least a first local coordination of benefits registry associated with a first entity comprising coverage information for a first set of members associated with the first entity and a second local coordination of benefits registry associated with a second entity comprising coverage information for a second set of members associated with the second entity that is different from the first set of members, wherein the computer program instructions, when executed by one or more physical processors of a computer, program the computer to:
obtain: (i) a first set of member information that describes a member covered by a first health plan; and (ii) a second set of member information that describes a member covered by a second health plan;
compare at least a portion of the first set of member information and at least a portion of the second set of member information;
determine that the first set of member information and the second set of member information relate to a first member that is covered by both the first health plan and the second health plan based on the comparison;
identify first coverage information that indicates a first responsibility of the first health plan to pay for at least a first portion of one or more medical expenses related to the first member based on the first set of member information, and second coverage information that indicates a second responsibility of the second health plan to pay for at least a second portion of the one or more medical expenses related to the first member based on the second set of member information;
generate, prior to payment of the one or more medical expenses by the first health plan or the second health plan, one or more coordination of benefits records that indicate that the first member is covered by both the first health plan and the second health plan based on the determination, wherein the one or more coordination of benefits records have a common data structure comprising (i) the first coverage information, (ii) the second coverage information, and (iii) a member identifier that identifies the first member;
update a central coordination of benefits registry maintained by the one or more physical processors based on the one or more coordination of benefits records, the central coordination of benefits registry storing coverage information on a per member basis, the coverage information including information indicating one or more health plans related to individual members and how medical expenses for the individual members are to be apportioned among the one or more health plans, wherein the central coordination of benefits registry includes coordination of benefits records having the common data structure for individual members that are covered by two or more health plans;
identify a first set of information from the central coordination of benefits registry for a first set of members associated with the first entity and a second set of information from the central coordination of benefits registry for a second set of members associated with the second entity;
transmit the first set of information to a device of the first entity to facilitate updating the first local coordination of benefits registry; and
transmit the second set of information to a device of the second entity to facilitate updating the second local coordination of benefits registry.

* * * * *